United States Patent [19]

Jacquot et al.

[11] Patent Number: 5,180,855
[45] Date of Patent: Jan. 19, 1993

[54] PROCESS FOR THE PREPARATION OF CITRAL

[75] Inventors: Roland Jacquot, Sainte Foy Les Lyon; Claude Mercier, Lyons, France

[73] Assignee: Rhone-Poulenc Nutrition Animale, Commentary, France

[21] Appl. No.: 690,829

[22] Filed: Apr. 26, 1991

[30] Foreign Application Priority Data

Apr. 27, 1990 [FR] France .................. 90 05380

[51] Int. Cl.$^5$ .............................. C07C 45/51
[52] U.S. Cl. ..................... 568/486; 568/449
[58] Field of Search .............. 568/449, 448, 486

[56] References Cited

U.S. PATENT DOCUMENTS

| 4,016,212 | 4/1977 | Leimgruber et al. ......... 568/486 |
| 4,288,636 | 9/1981 | Nissen et al. ............... 568/486 |

FOREIGN PATENT DOCUMENTS

| 0010235 | 4/1980 | European Pat. Off. . |
| 0021074 | 1/1981 | European Pat. Off. ...... 568/448 |
| 0287956 | 10/1988 | European Pat. Off. . |
| 6095142 | 8/1981 | Japan .................. 568/449 |
| 61274599 | 6/1988 | Japan . |

Primary Examiner—Werren B. Lone
Attorney, Agent, or Firm—Finnegan, Henderson, Farabow, Garrett, and Dunner

[57] ABSTRACT

A process for the preparation of citral by the cracking of prenal diprenyl acetal in a vapor phase in the presence of a heterogeneous type of acid catalyst.

12 Claims, No Drawings

PROCESS FOR THE PREPARATION OF CITRAL

BACKGROUND OF THE INVENTION

Field of the Invention

The present invention relates to a process for the preparation of citral. More particularly, it relates to a process for the preparation of citral by cracking of prenal diprenyl acetal in a vapor phase.

The citral thus obtained is useful as an intermediate in the synthesis of vitamin A. It can also be used for its aromatic properties.

The preparation of citral by cracking of prenal diprenyl acetal in a liquid phase is disclosed in the prior art. For example, the preparation of aldehydes containing $\alpha,\beta$-ethylene bonds by reacting an aldehyde containing an $\alpha,\beta$-ethylene bond and an allyl alcohol at a high temperature in the liquid phase is disclosed in French Patent No. 2,160,125. The aldehyde containing an $\alpha,\beta$-ethylene bond may be 3,3-dimethylacrolein, which is also known by the name prenal, and the allyl alcohol may be 3-methyl 2-buten-1-ol known by the name prenol.

The condensation reaction is preferably carried out in the presence of an acid catalyst at a temperature between 100° and 250° C. The acid used as a catalyst is preferably selected from inorganic acids such as sulphuric, phosphoric, halogenated, nitric, sulphurous, phosphorous, perchloric, boric, silicic, and salts of acids containing a dissociable hydrogen. Organic acids can also be used. The quantity of acid used in the case of an inorganic acid with a pK of 0 to about 3 is preferably between 0.01 and 0.5%. Other patents, such as French Patent No. 1,582,515 describe variants and improvements to this type of process.

The preparation of citral by heating diprenyl acetal in the presence of phosphoric acid and an inert liquid which has, at the pressure of the reaction, a boiling point greater than that of prenol and lower than that of citral, is disclosed in U.S. Pat. No. 4,288,636. The inert liquid is preferably 3,3,7-trimethyl-4-oxa-1,6-octadiene. The quantity of phosphoric acid used is between 0.001 and 0.5 % by weight, and preferably between 0.005 and 0.05 % by weight.

However, these liquid phase processes for preparing citral have many disadvantages. In particular, because of the large volume of liquid which must be used, the difficulty or even the impossibility of carrying out the reactions continuously, and also the high cost of the operations, these processes are difficult to exploit industrially.

To avoid these disadvantages, the present invention provides a process for the preparation of citral by cracking prenal diprenyl acetal in a vapor phase, in the presence of a heterogeneous type of acid catalyst.

An important aspect of the present invention resides in the choice of the catalyst, which is important to the efficacy of the reaction. We have observed that in the presence of catalysts exhibiting an acidity which is too high, the citral was converted to secondary cyclic products such as para-cymene. This reaction of degradation of citral has been previously observed by Clark et al.; Tetrahedron, Vol. 33 p. 2187, (1977); who identified 14 cyclic products obtained from citral in acid media. More particularly, the authors studied the degradation products of citral in the presence of hydrochloric acid, at pH values between 2.4 and 3.2. They showed the presence of novel products, and proposed a reaction pathway. However, the list of products obtained is not exhaustive, and that products not yet identified must be formed.

SUMMARY OF THE INVENTION

The present invention overcomes the problems and disadvantages of the prior art by carrying out the reaction for the preparation of citral from prenal diprenyl acetal in the vapor phase and in the presence of catalysts which possess sufficiently high acidity to allow cracking of the acetal, but not too high in order to avoid converting the citral to other or secondary products. It has been found necessary to use a catalyst which has an appropriate acidity in order to obtain high yields of citral. Under these conditions, the catalyst used is a heterogeneous type of acid catalyst, selected on the basis of its behavior during a test reaction involving the conversion of citral to cyclic products.

This test reaction consists of introducing into a reactor, 1 ml of catalyst between two 5 ml quartz beds. The catalyst is then activated by heating it at 300° C. for one hour under a stream of nitrogen at a flow rate of 3 liters per hour. Finally, the citral is injected at a rate of 4 ml per hour, over one hour, while at the same time condensing the gas produced by the reaction. The condensate thus obtained is analyzed by gas chromatography. Catalysts with the correct acidity which may be used in the present invention are ones that do not convert more than 30% of the citral to secondary products under these test conditions.

DESCRIPTION OF THE PREFERRED EMBODIMENTS

Reference will now be made in detail to present preferred embodiments of the invention. In the examples and throughout the specification and claims, all parts and percentages are by weight unless otherwise specified.

The conversion of prenal diprenyl acetal to citral can be shown schematically as follows:

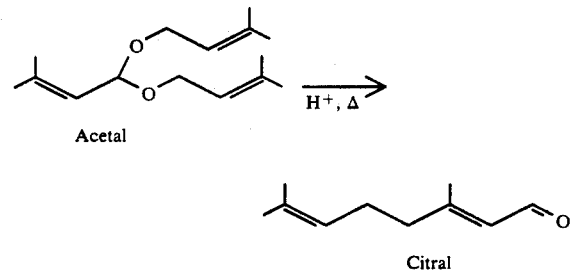

One group of heterogeneous acid catalysts which satisfy the above described test conditions are those that possess a cation exchange capacity, such as zeolites. Commercial zeolites, to which some modifications are optionally made, can be used in this respect. Preferably, either the 3Å molecular sieve or sodium-exchanged mordenite is used.

Other catalysts include oxides of metals in columns IIIb to VIb of the periodic table of elements. Preferably, the oxides are selected from oxides of zirconium, molybdenum, vanadium or cerium.

The heterogeneous acid catalysts may also be salts, such as phosphate, silicate, or chromite salts. Preferably, calcium silicate, lithium phosphate, or copper chromite are used.

The process for cracking the acetal in the vapor phase in accordance with the present invention is preferably carried out at a temperature between the boiling temperature of prenal diprenyl acetal, i.e., about 230° C., and about 400° C., and more preferably between 250° C. and 350° C. The process can be also carried out under reduced pressure or at atmospheric pressure.

One practical method of carrying out the present invention comprises introducing a desired quantity of catalyst into a reactor and placed between two quartz beds in order to enhance its contact with the reagents. The temperature of the reactor is then increased to a predetermined value, preferably between the boiling temperature of acetal and about 400° C., in order to activate the catalyst. Acetal is then injected at the desired rate in the presence of an inert gas such as helium, argon or nitrogen. The gases are then condensed, and the products are analyzed.

Preferably, for every 1 ml of catalyst, the inert gas is introduced at a rate of from 0.1 to 10 liters per hour, and the acetal can be injected at a liquid flow rate of up to 10 ml per hour, and more preferably up to 5 ml per hour.

The present invention will be more completely described with the help of the following examples, which should be considered as being illustrative and non-restrictive.

EXAMPLE 1

Test of acid catalysts

Into a glass cylindrical reactor 18 mm in diameter, is introduced 1 ml of catalyst between two 5 ml quartz beds. The catalyst is activated at 300° C. for one hour under a stream of nitrogen at 3 liters per hour. The heating is carried out in an electric oven. Citral is then injected at a rate of 4 ml per hour, over one hour, using a push syringe. The gas is condensed, and the condensate is analyzed by gas chromatography. The results of this test are shown in Table 1.

In the Tables, certain abbreviations are used. These abbreviations are defined as follows:

CY = conversion yield : corresponds to the number of moles of the compound initially present, minus the number of moles of the compound remaining at the end, divided by the number of moles initially present.

Ay = actual yield : corresponds to the number of moles obtained over the number of moles used.

O = a catalyst whose acidity corresponds to the requirements of the process in accordance with the invention.

N = a catalyst whose acidity is too high for the process in accordance with the invention.

TABLE 1

| Catalyst | CY % citral | AY % p-cymene | Cyclized other | Acidity O/N |
|---|---|---|---|---|
| Lithium phosphate | 14 | 0-1 | 10 | O |
| Molecular sieve 3Å | 22 | 0-1 | 20 | O |
| ZrO$_2$, hydrated | 13 | 0-1 | 12 | O |
| Mordenite Na+ | 28 | 0-1 | 21 | O |
| Mordenite H | 54 | 14 | 21 | N |
| Cu chromite | 20 | 0-1 | 12 | O |
| ZM 980 Zeocat | 81 | 26 | 18 | N |
| HZSM 5 | 47 | 6 | 14 | N |

Catalysts which convert less than 30% of the citral introduced to secondary products have the acidity required for use in the process according to the invention. On the other hand, the other heterogeneous types of acid catalysts which convert more than 30% of the citral to secondary products cannot be used in the process of the present invention.

EXAMPLE 2

Into a tubular glass reactor 18 mm in diameter, 1 ml of catalyst is introduced between two 5 ml quartz beds. The catalytic bed is preheated for 1 hour at 350° C. under a nitrogen stream of 8 liters per hour. Using a push syringe, prenal diprenyl acetal is injected at a liquid flow rate of 2 ml per hour. After one hour of reaction in the vapor phase, analysis of the condensate by gas chromatography gives the CY of acetal and the AY of citral. The results of this test are shown in Table 2.

TABLE 2

| Catalyst | CY % acetal | AY % citral |
|---|---|---|
| Mordenite Na+ | 100 | 30 |
| Molec. sieve 3Å | 80 | 30 |
| Vanadium oxide | 84 | 22 |
| Lithium phosphate | 96 | 30 |
| Calcium silicate | 95 | 27 |
| Copper chromite | 100 | 24 |
| Zirconium dioxide | 100 | 30 |
| Molybdenum oxide | 80 | 25 |
| Cerium oxide | 95 | 25 |
| ZrO$_2$ + Cr | 75 | 22 |

EXAMPLE 3

Into a tubular glass reactor 18 mm in diameter, 10 ml of catalyst is introduced. The catalytic bed is preheated at 250° C. under a nitrogen stream of 0.6 liter per hour. Using a push syringe, prenal diprenyl acetal is injected at a liquid flow rate of 2 ml per hour. After one hour or reaction in the gas phase, analysis of the condensate by gas chromatography gives the CY of acetal and the AY of citral. The results of this test are shown in Table 3.

TABLE 3

| Catalyst | CY % acetal | AY % citral |
|---|---|---|
| Sieve 3Å | 100 | 85 |
| Mordenite Na+ | 85 | 36 |
| Zirconium dioxide | 100 | 54 |

It will be apparent to those skilled in the art that various modifications and variations can be made in the present invention without departing from the scope or spirit of the invention. Thus, it is intended that the present invention cover the modifications and variations of this invention provided they come within the scope of the appended claims and their equivalent.

What is claimed is:

1. A process for the preparation of citral, comprising cracking prenal diprenyl acetal in the vapor phase in the presence of a heterogeneous acid catalyst, said acid catalyst being selected from a group of catalysts that do not convert more than 30 % of citral to other products when a stream of citral at a flow rate of 4 ml/h is introduced into a reactor containing 1 ml of said catalyst between two 5 ml quartz beds heated to a temperature of 300° C. for one hour in the presence of a stream of nitrogen at a flow rate of 3 l/h, wherein the catalyst is selected from the group consisting of a zeolite, an oxide of a metal selected from columns IIIb to VIb of the periodic table of elements and phosphate, silicate or chromite salts.

2. A process for the preparation of citral which comprises cracking prenal diprenyl acetal in the vapor phase in a reactor in the presence of a heterogeneous acid catalyst selected from the group consisting of a zeolite, an oxide of a metal selected from columns IIIb to VIb of the periodic table of elements, calcium silicate, lithium phosphate and copper chromite.

3. The process of claim 2, wherein the zeolite is selected from sodium-exchanged mordenite and a 3Å molecular sieve zeolite.

4. The process of claim 2, wherein the oxide is selected from oxides of zirconium, molybdenum, vanadium and cerium.

5. The process of claim 2, wherein said process is carried out at a temperature between the boiling temperature of prenal diprenyl acetal and about 400° C.

6. The process of claim 5, wherein said temperature is between 250° C. and 350° C.

7. The process of claim 2, wherein said process is carried out at a pressure less than or equal to atmospheric pressure.

8. The process of claim 2, wherein for every 1 ml of catalyst, prenal diprenyl acetal is introduced into the reactor at a liquid flow rate of up to 10 ml per hour.

9. The process of claim 8, wherein said flow rate is up to 5 ml per hour.

10. The process of claim 2, wherein the reaction is carried out in the reactor in the presence of an inert gas.

11. The process of claim 10, wherein for every 1 ml of catalyst, the inert gas is introduced at a rate of from 0.1 to 10 liters per hour.

12. The process of claim 11, wherein the inert gas is selected from the group consisting of helium, argon or nitrogen.

* * * * *